United States Patent
Kahlert et al.

(10) Patent No.: US 10,202,575 B2
(45) Date of Patent: Feb. 12, 2019

(54) SYSTEM FOR SWITCHING OVER THE EXHAUST AIR OF A BIOREACTOR

(71) Applicant: Sartorius Stedim Biotech GmbH, Goettingen (DE)

(72) Inventors: Wolfgang Kahlert, Koerle (DE); Ralf Hartmann, Doeringsdorf (DE); Bernward Husemann, Goettingen (DE)

(73) Assignee: Sartorius Stedim Biotech GmbH (DE)

( * ) Notice: Subject to any disclaimer, the term of this patent is extended or adjusted under 35 U.S.C. 154(b) by 0 days.

(21) Appl. No.: 14/787,323

(22) PCT Filed: Mar. 22, 2014

(86) PCT No.: PCT/EP2014/000782
§ 371 (c)(1),
(2) Date: Oct. 27, 2015

(87) PCT Pub. No.: WO2014/177240
PCT Pub. Date: Nov. 6, 2014

(65) Prior Publication Data
US 2016/0108354 A1    Apr. 21, 2016

(30) Foreign Application Priority Data

May 3, 2013  (DE) .................... 20 2013 004 096 U

(51) Int. Cl.
*C12M 1/34* (2006.01)
*C12M 1/00* (2006.01)
(Continued)

(52) U.S. Cl.
CPC ............ *C12M 41/40* (2013.01); *C12M 23/28* (2013.01); *C12M 29/04* (2013.01); *C12M 29/20* (2013.01);
(Continued)

(58) Field of Classification Search
CPC ...... C12M 29/20; C12M 41/12; C12M 41/40; B01D 35/147
See application file for complete search history.

(56) References Cited

U.S. PATENT DOCUMENTS

| 2004/0096943 A1 | 5/2004 | Marx et al. |
| 2005/0106720 A1 | 5/2005 | Nagel-Heuer et al. |

(Continued)

FOREIGN PATENT DOCUMENTS

| CA | 2 064 402 | 10/1993 |
| DE | 42 36 856 | 5/1994 |

(Continued)

OTHER PUBLICATIONS

International Search Report.
International Preliminary Report on Patentability dated Nov. 3, 2015.

*Primary Examiner* — Jonathan M Hurst
(74) *Attorney, Agent, or Firm* — Gerald E. Hespos; Michael J. Porco; Matthew T. Hespos

(57) ABSTRACT

A system (1) is provided for switching over exhaust air of a bioreactor (2) that has a disposable container (3). The system (1) has at least two exhaust air ducts (4, 5) connecting the disposable container (3) to exhaust air filters (6, 7, 18, 18'). A valve (8) is disposed in at least one of the at least two exhaust air ducts (4, 5) and enables the associated exhaust air filter (6, 7, 18, 18') to be freed.

12 Claims, 8 Drawing Sheets

(51) Int. Cl.
*C12M 1/12* (2006.01)
*C12M 1/36* (2006.01)

(52) U.S. Cl.
CPC ............ *C12M 37/02* (2013.01); *C12M 37/04* (2013.01); *C12M 41/48* (2013.01)

(56) References Cited

U.S. PATENT DOCUMENTS

| | | | |
|---|---|---|---|
| 2008/0213874 A1* | 9/2008 | Mitchell | G01F 23/14 435/287.1 |
| 2009/0155885 A1 | 6/2009 | Bartsch | |
| 2009/0269849 A1 | 10/2009 | Lee et al. | |
| 2010/0170400 A1 | 7/2010 | van den Boogard et al. | |
| 2011/0159539 A1 | 6/2011 | Eisenkraetzer et al. | |
| 2011/0198255 A1 | 8/2011 | Baumfalk et al. | |
| 2011/0207170 A1 | 8/2011 | Niazi | |
| 2011/0207218 A1 | 8/2011 | Staheli et al. | |
| 2012/0018654 A1* | 1/2012 | Wennberg | F16K 7/06 251/9 |
| 2012/0074069 A1* | 3/2012 | Ripley | B01D 35/1435 210/741 |
| 2012/0132548 A1 | 5/2012 | Galliher et al. | |
| 2014/0011270 A1* | 1/2014 | Chotteau | C12M 23/14 435/326 |
| 2015/0232799 A1 | 8/2015 | Reif et al. | |

FOREIGN PATENT DOCUMENTS

| | | |
|---|---|---|
| DE | 103 04 236 | 8/2003 |
| DE | 102 08 311 | 9/2003 |
| DE | 10 2006 004 157 | 8/2007 |
| DE | 10 2008 013 899 | 9/2009 |
| DE | 10 2008 033 286 | 1/2010 |
| DE | 10 2009 003 972 | 7/2010 |
| DE | 10 2012 017 972 | 3/2014 |
| EP | 0 507 073 | 10/1992 |
| GB | 26 773 | 7/1911 |
| WO | 2008/135991 | 11/2008 |
| WO | 2010/046029 | 4/2010 |
| WO | 2011/041508 | 4/2011 |
| WO | 2012/049290 | 4/2012 |
| WO | 2011/115586 | 8/2012 |
| WO | 2013/053779 | 4/2013 |

* cited by examiner

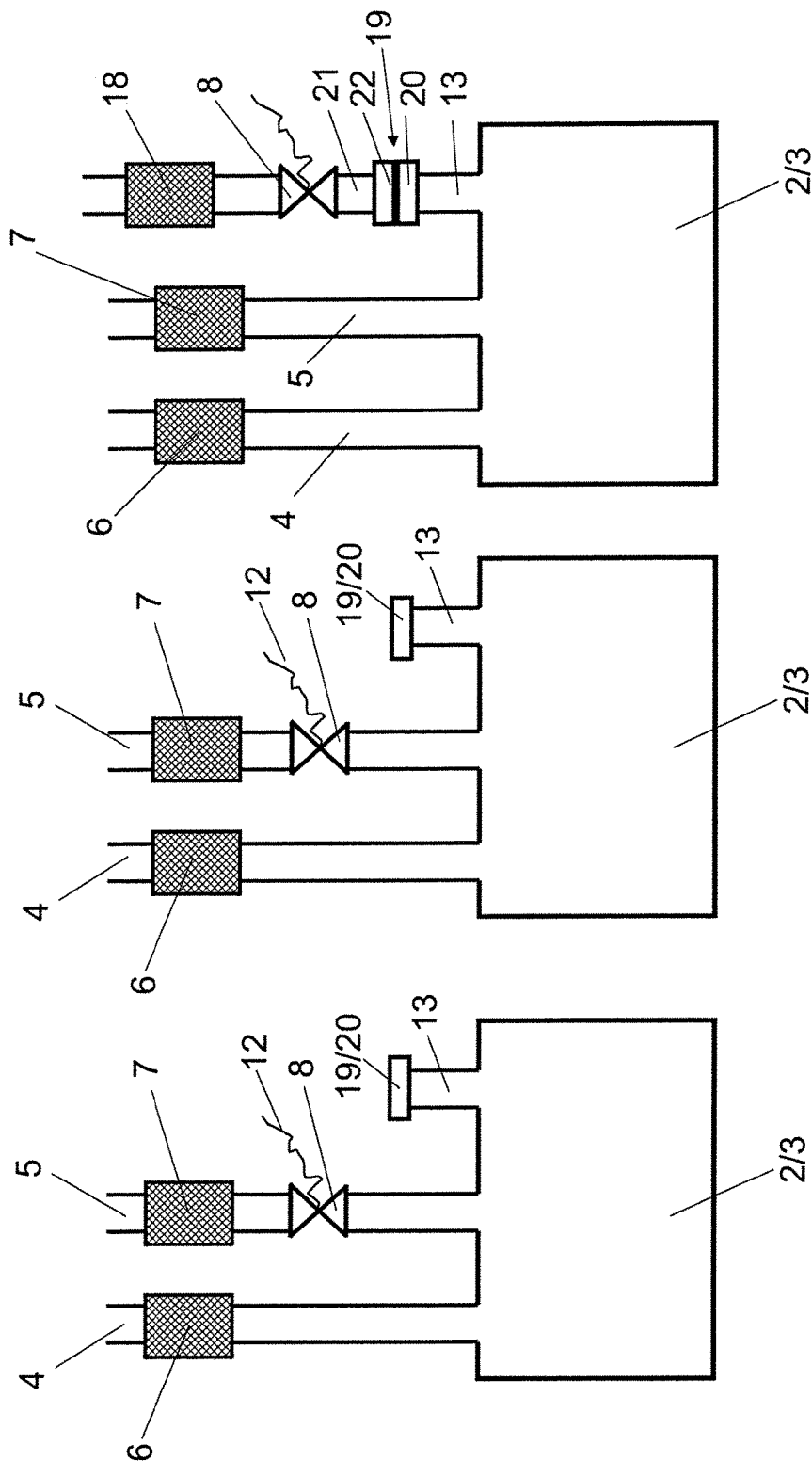

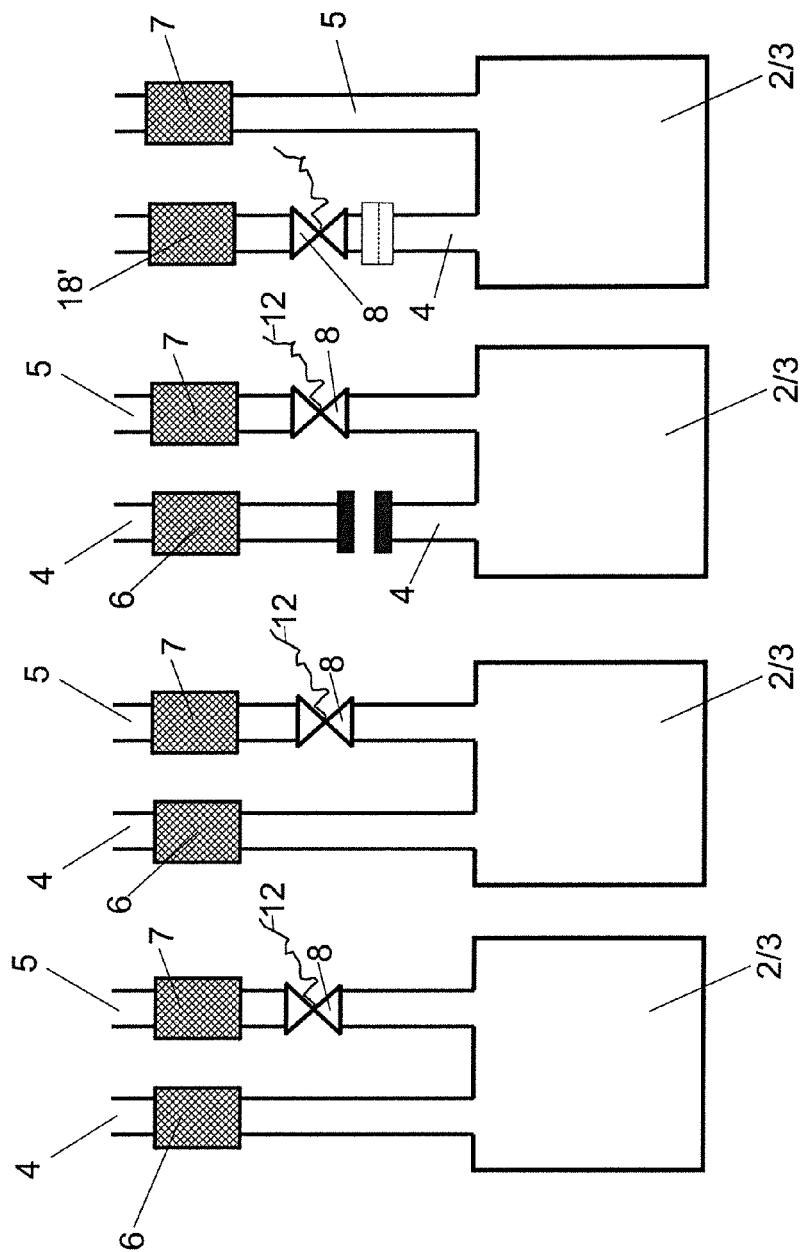

SYSTEM FOR SWITCHING OVER THE EXHAUST AIR OF A BIOREACTOR

BACKGROUND

1. Field of the Invention

The invention relates to a system for switching over the exhaust air of a bioreactor, the disposable container of which is connected by means of at least two exhaust air ducts to exhaust air filters.

2. Description of the Related Art

Bioreactors with exhaust air ducts usually have an exhaust air filter in the exhaust air duct for protection against contamination inwards and outwards. In use, these exhaust air filters can become blocked, which leads to an undesirable rise in pressure in the bioreactor. In order to prevent undesirable rupture of a disposable container, for example, the process must be interrupted and the exhaust air filter must be replaced.

A bioreactor system is known from US 2009/0269849 A1, in which the container in the form of a bag is connected by means of two exhaust air ducts to exhaust air filters. In this case pressure equalization can take place by means of the exhaust air ducts with the exhaust air filters.

A disadvantage of this is that the use of two exhaust air ducts with two exhaust air filters increases the service life until a blockage occurs, but a blockage cannot be prevented. In the event of a blockage the process must also be interrupted in this case.

Furthermore, a bioreactor system is known from US 2011/0207218 A1, which comprises a bioreactor in the form of a bag, wherein a gas discharge line is connected by means of an exhaust air cooler in the form of a bag to two exhaust air ducts branching off from the exhaust air cooler. The exhaust air ducts themselves each have a sterile filter.

In this case it is a disadvantage that a blockage of a filter can be caused both by moist exhaust air and also by particles. For this reason an exhaust air cooler cannot always prevent a blockage and it may then be necessary to change the filters. Here too the process must be interrupted.

The object of the present invention is therefore to prevent a pressure rise in the disposable container due to blockage of the exhaust air filters and to avoid interruption of the process.

SUMMARY

The invention relates to a system for switching over the exhaust air of a bioreactor. The bioreactor includes a disposable container connected by at least two exhaust air ducts to exhaust air filters. A valve is disposed in at least one of the at least two exhaust air ducts and enables the associated exhaust air filter to be freed.

The valve is disposed upstream or downstream of the exhaust air filter and ensures that the exhaust air filter disposed upstream or downstream of the valve is unblocked at the time of opening the valve. The valve is opened when a specific pressure is reached as a result of blockage of the first exhaust air filter and the system is switched over to the second exhaust air filter.

In this case the exhaust air ducts can be connected separately to the disposable container. However, the exhaust air ducts can be connected to the disposable container by a distributor piece. A combination of different exhaust air ducts can be arranged in addition to a plurality of separate exhaust air ducts and exhaust air ducts that are connected by a distributor piece to the disposable container to increase the number of exhaust air filters.

At least one further exhaust air duct may be connected to the disposable container and may be closed at its free end by a part of a two-part sterile connector. If required, a further exhaust air filter and a valve can then be connected by means of the sterile connector.

Sensors may be provided in the exhaust air ducts and/or in air supply ducts to the disposable container. The sensors enable the pressure in the disposable container to be determined.

A regulating and control unit also may be provided. The regulating and control unit may be connected by control lines to the valve and/or may be connected to the sensors by sensor lines. Due to the regulating and control unit, when a predetermined limiting pressure is reached a switching over of the exhaust air can take place automatically, as a further exhaust air filter is connected by opening of the valve associated with it. Even if the valves are preferably disposed upstream of the exhaust air filters, it is still also possible to dispose the valves downstream of the exhaust air filters.

An exhaust air cooler may be disposed between the disposable container and the exhaust air filter. The exhaust air cooler can reduce the blockage of exhaust air filters due to moisture.

Further features of the invention are disclosed by the following detailed description and the appended drawings, in which preferred embodiments of the invention are illustrated by way of example.

BRIEF DESCRIPTION OF THE DRAWINGS

FIG. 7 shows an exhaust air system of a bioreactor at the start of the process, similar to FIG. 1, with an additional exhaust air duct which is closed by a first part of a two-part sterile connector.

FIG. 8 shows the system for switching over the exhaust air according to FIG. 7 with the blocked first filter and the opened valve disposed upstream of the second filter.

FIG. 9 shows the system for switching over the exhaust air according to FIG. 8 with the second part fitted onto the first part of the two-part sterile connector with the closed valve and the further exhaust air filter disposed downstream.

FIG. 10 shows the start of the process of a system for switching over the exhaust air according to FIG. 1 with a closed valve.

FIG. 11 shows the system according to FIG. 10 with the blocked first filter and the opened valve disposed upstream of the second filter.

FIG. 12 shows the system according to FIG. 11 with the welded and separated first exhaust air duct.

FIG. 13 shows the system for switching over the exhaust air according to FIG. 12 with a new hose piece welded on with a filter and closed valve.

DETAILED DESCRIPTION

Figure 1:
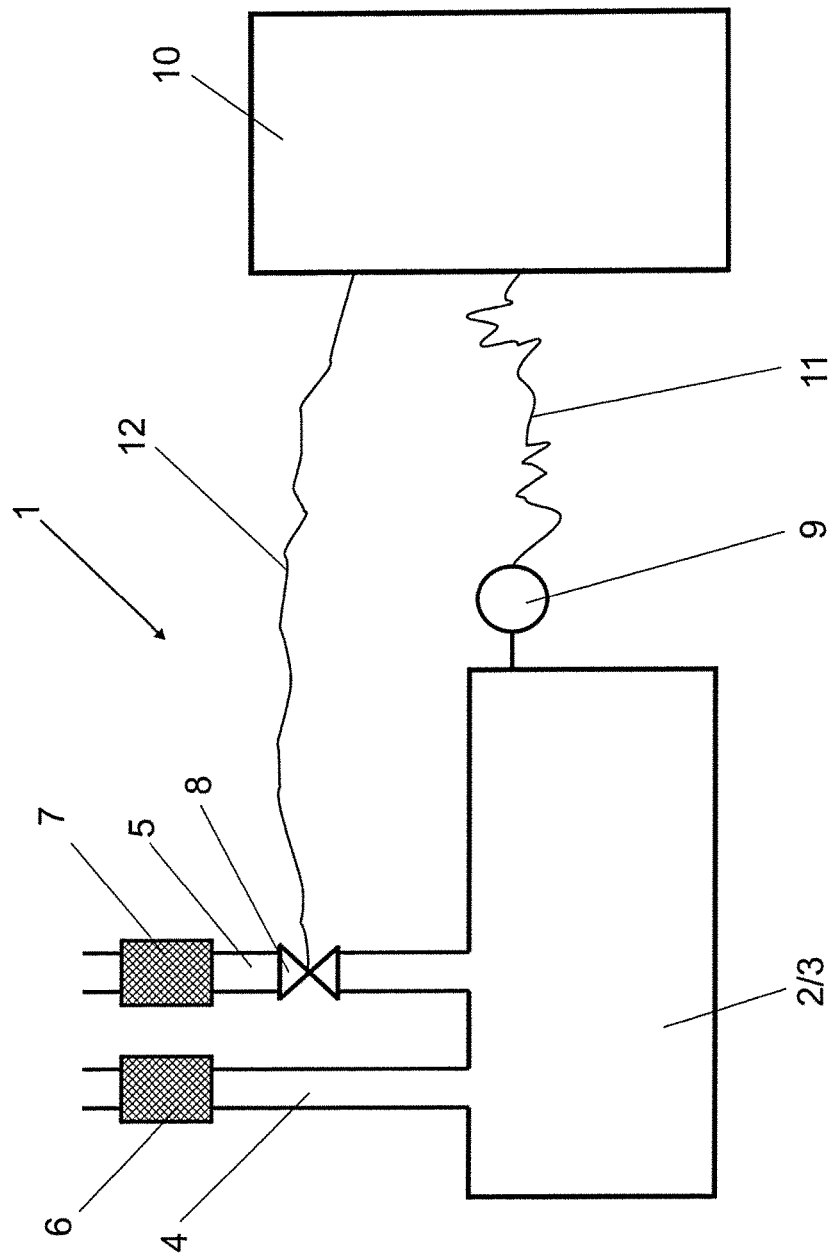
FIG. 1 shows a basic side view of a system for switching over the exhaust air of a bioreactor with separate exhaust air ducts with exhaust air filters and a regulating and control unit.

A system 1 for switching over the exhaust air of a bioreactor 2 consists predominantly of the disposable container 3, exhaust air ducts 4, 5 and exhaust air filters 6, 7.

According to the exemplary embodiments of FIGS. 1 to 4 and 7 to 13, the exhaust air ducts 4, 5 are connected separately to the disposable container 3. According to the exemplary embodiment of FIG. 1, a valve 8 is disposed in the second exhaust air duct 5 between the disposable container 3 and the second exhaust air filter 7. The valve 8 can be designed for example as a pinch valve. The use of a pinch valve has the advantage that it can be fitted from the exterior onto an exhaust air duct 5 in the form of a flexible hose and, after blocking of the filter, can be used at a different location. However, in principle it is also possible to design the valves 8 as single-use valves. According to the exemplary embodiment of FIG. 1 the interior of the disposable container 3 is connected to a sensor 9 in the form of a pressure sensor.

A regulating and control unit 10 is connected by means of a sensor line 11 to the sensor 9. The regulating and control unit 10 is connected by means of a control line 12 to the valve 8. By means of the regulating and control unit 10 the valve 8 in the second exhaust air duct 5 is opened as a function of the pressure in the disposable container 3, so that in the event of a pressure rise as a result of blockage of the first exhaust air filter 6 the second exhaust air filter 7 is freed and thus the exhaust air is switched over to the second filter 7.

Figure 2:
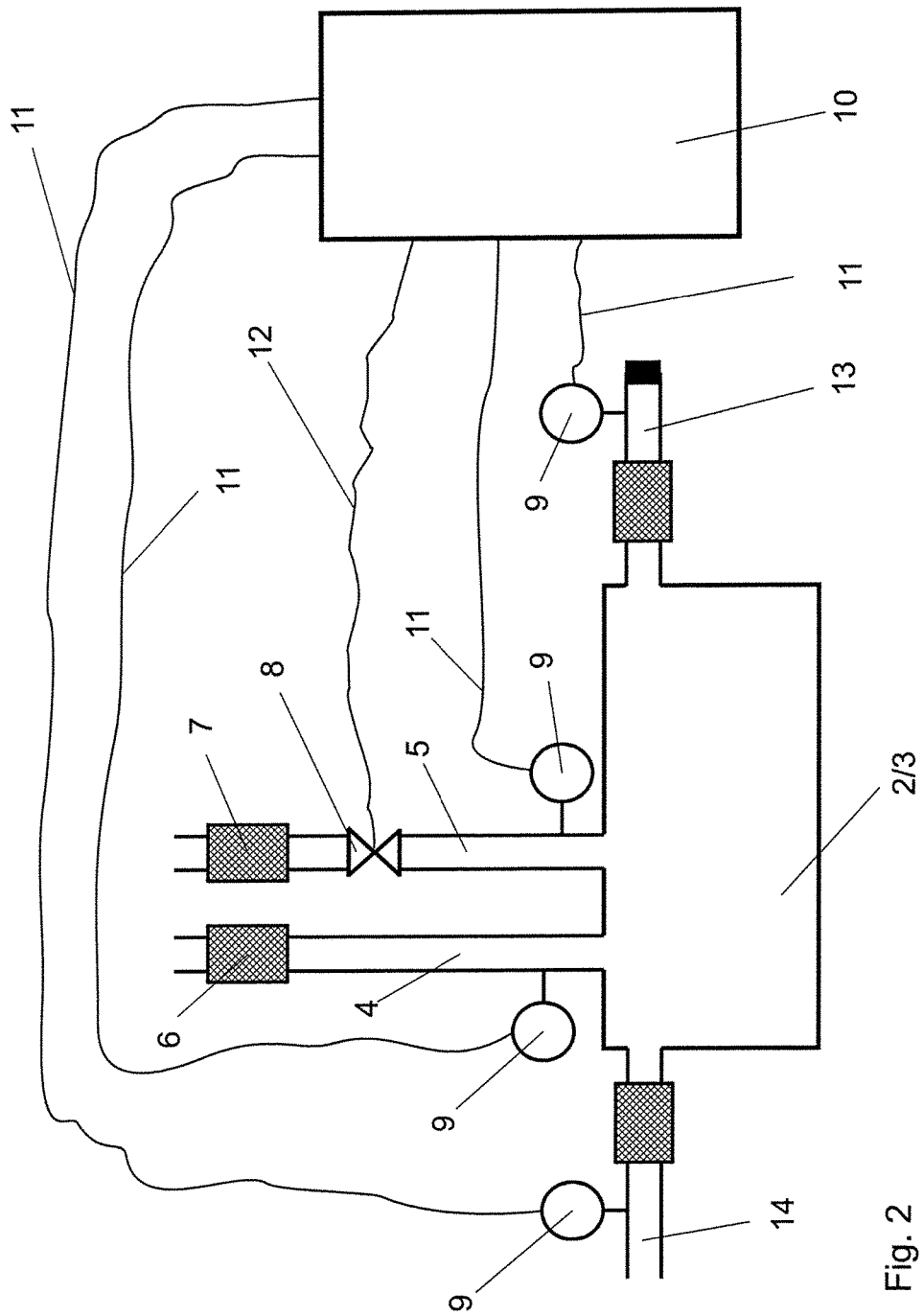
FIG. 2 shows a further exhaust air system corresponding to FIG. 1 with additional sensors in the exhaust air ducts and in an air supply duct to the disposable container.

According to the exemplary embodiment of FIG. 2, the sensors 9 can also be disposed in the exhaust air ducts 4, 5 and in a third exhaust air duct 13. Finally, the sensor 9 can also be disposed as a pressure sensor in an air supply duct 14 to the disposable container 3.

Figure 3:
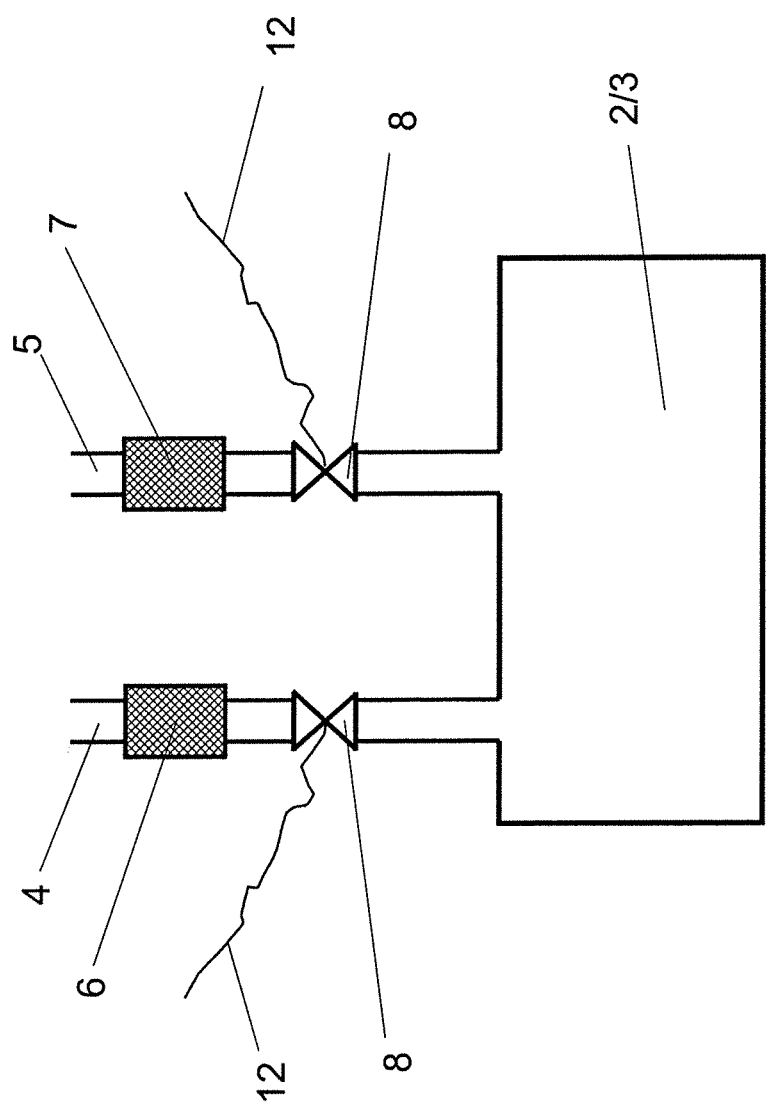
FIG. 3 shows a further exhaust air system corresponding to FIG. 1 with an additional valve in the first exhaust air duct and a regulating and control unit (not shown).
Figure 4:
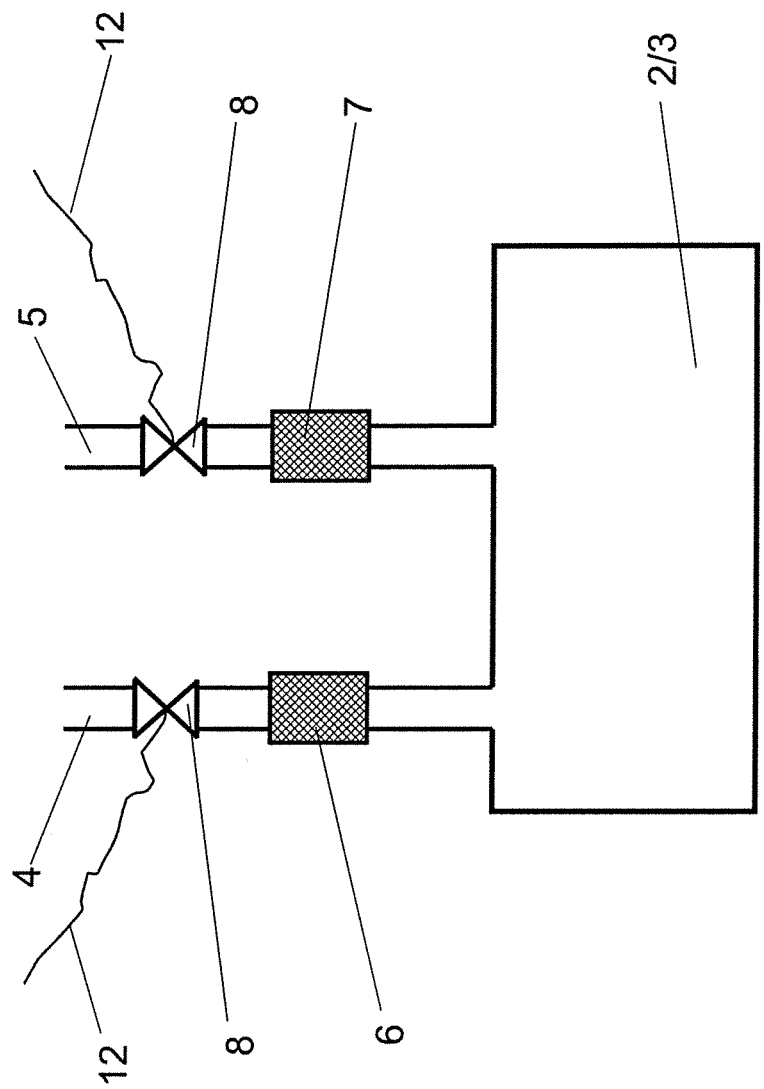
FIG. 4 shows a further exhaust air system corresponding to FIG. 3 but with valves disposed downstream of the exhaust air filters in the exhaust air flow direction.

According to the exemplary embodiment of FIG. 3, a valve 8 is disposed in each case facing the disposable container 3 upstream of both the first exhaust air filter 6 and also the second exhaust air filter 7. According to the exemplary embodiment of FIG. 4, the valves 8 can also be disposed facing away from the disposable container 3 downstream of the exhaust air filters 6, 7.

Figure 5:
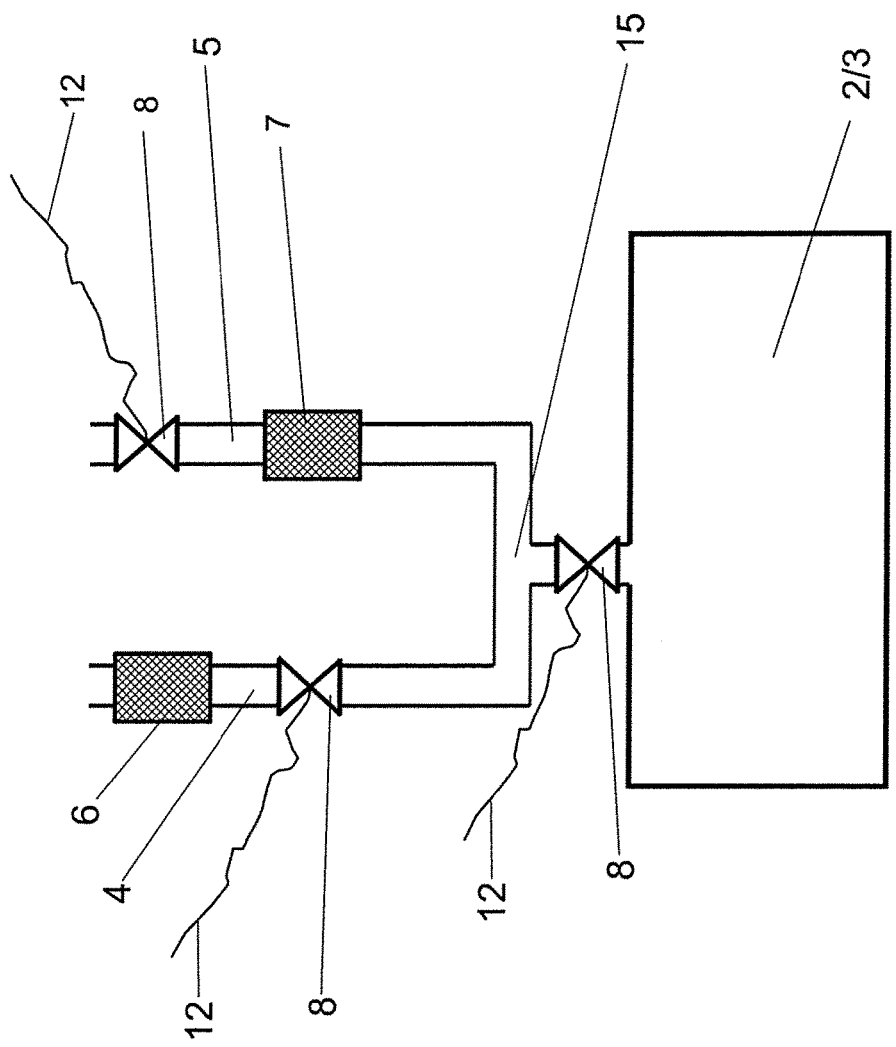
FIG. 5 shows a further system for switching over the exhaust air with exhaust air ducts which are connected by means of a distributor piece to the disposable container, a valve being disposed in the distributor piece.
Figure 6:
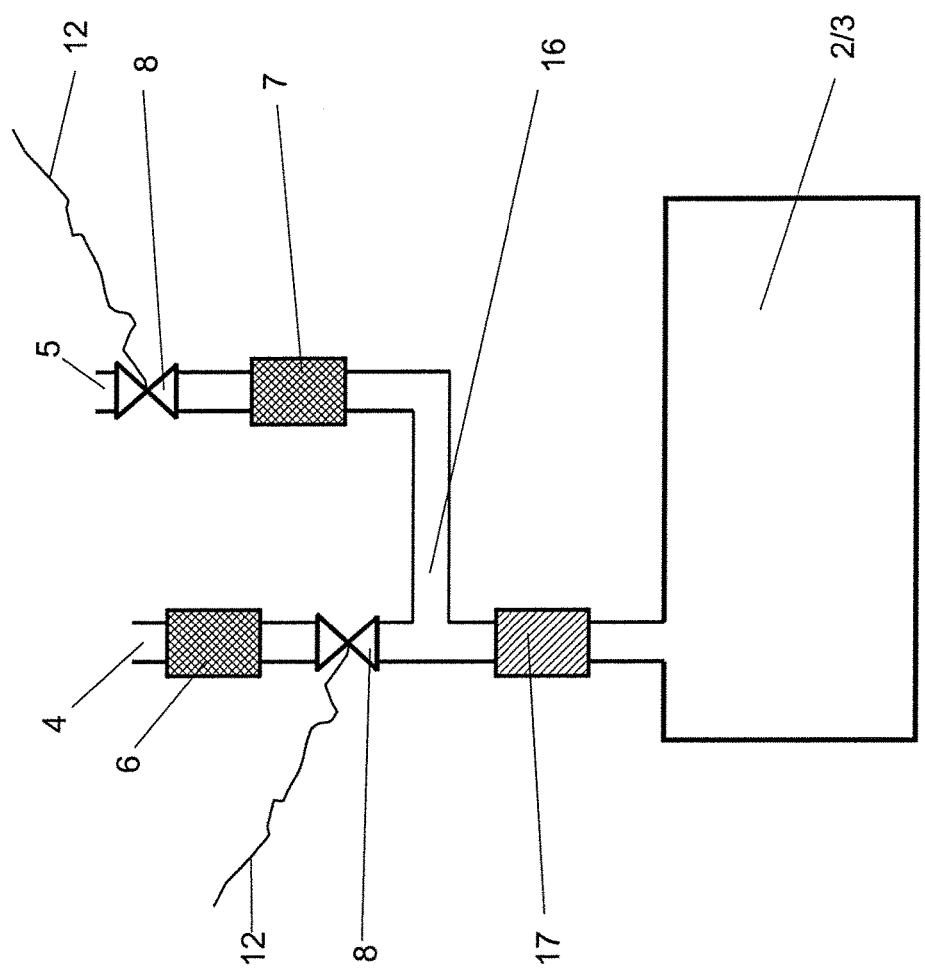
FIG. 6 shows a further system for switching over the exhaust air, in which the exhaust air ducts are connected by means of a distributor piece to the disposable container, an exhaust air cooler being disposed between the distributor piece and the disposable container.

According to FIGS. 5, 6, the exhaust air ducts 4, 5 can also be connected by means of a distributor piece 15, 16 to the disposable container 3. According to the exemplary embodiment of FIG. 5, a valve 8 is disposed between the distributor piece 15 and the disposable container 3. According to the exemplary embodiment of FIG. 6, an exhaust air cooler 17 is disposed between the distributor piece 16 and the disposable container 3.

FIGS. 7 to 9 show a process sequence in which a subsequent unused third exhaust air filter 18 (or further exhaust air filters) is connected by means of a two-part sterile connector 19 and a valve 8 in the form of a hose pinch valve. FIG. 7 shows the start of the process with a closed valve 8 in the second exhaust air duct 5, wherein the exhaust air is drawn off by means of the first exhaust air duct 4 with the unblocked first exhaust air filter 6. The third exhaust air duct 13 is closed by a first part 20 of the two-part sterile connector 19. FIG. 8 shows the process with the blocked first exhaust air filter 6 and the opened valve 8 in the second exhaust air duct 5. Thus the exhaust air is switched over from the first exhaust air duct 4 to the second exhaust air duct 5. FIG. 9 shows the installed third exhaust air filter 18, which has been connected by means of a connecting line 21 and a second part 22 of the sterile connector 19 with the first part 20. The valve 8 designed as a hose pinch valve has been fitted from the second exhaust air duct 5 onto the connecting line 21 of the third exhaust air duct 13 and is closed. The exhaust air duct 4 does not require any valve since the first exhaust air filter 6 is blocked, and the second exhaust air filter 7 does not require any valve since the second exhaust air filter 7 is operational. The valve 8 is only opened when the second exhaust air filter 7 is blocked.

FIGS. 10 to 13 show a further process in which a new unused filter can be connected at a later stage in place of a blocked filter. FIG. 10 also shows the start of the process with an unblocked first exhaust air filter 6 and a still unused second exhaust air filter 7 with a valve 8 connected upstream in the closed position. The valve 8 in the exemplary embodiment according to FIGS. 10 to 13 is likewise formed as a hose pinch valve. In FIG. 11 the first exhaust air filter 6 is blocked and the second exhaust air filter 7 with the valve 8 opened is operational. FIG. 12 shows the first exhaust air filter 6, which is separated in a sterile manner from the disposable container 3 by sealing. The valve 8 in the exhaust air duct 5 is also open. FIG. 13 shows a third exhaust air filter 18', which has been connected by means of welding in a sterile manner to the remaining first exhaust air duct 4 and of which the valve 8 is closed because the second exhaust air filter 7 is not yet blocked, and which can be set in operation later by opening of the valve 8 if the second exhaust air filter 7 should become blocked in the further course of the process.

In the exemplary embodiments according to FIGS. 7 to 13 the valves 8 can also be designed as single-use valves.

Naturally the embodiments discussed in the specific description and shown in the drawings only constitute illustrative exemplary embodiments of the present invention. In the light of the present disclosure the person skilled in the art is offered a wide range of possible variations.

LIST OF REFERENCES

1 system for switching over the exhaust air
2 bioreactor
3 disposable container of 2
4 first exhaust air duct
5 second exhaust air duct
6 first exhaust air filter
7 second exhaust air filter
8 valve
9 sensor
10 regulating and control unit
11 sensor line
12 control line
13 third exhaust air duct
14 air supply duct
15 distributor piece
16 distributor piece
17 exhaust air cooler
18, 18' third exhaust air filter
19 sterile connector 20 first part of the sterile connector 19
21 connecting line
22 second part of the sterile connector 19

The invention claimed is:

1. A system (1) for switching over exhaust air of a bioreactor (2), the bioreactor (2) having a disposable container (3), the system (1) comprising:
    an air supply duct (14) extending into the disposable container (3),
    at least first and second exhaust air ducts (4, 5) extending from the disposable container (3),
    at least first and second exhaust air filters (6, 7, 18, 18') communicating respectively with the first and second exhaust air ducts (4, 5),
    at least one exhaust air pressure sensor (9) communicating with at least one of the exhaust air ducts (4, 5),
    an air supply pressure sensor (9) communicating with the air supply duct (14)
    a valve (8) mounted to the second exhaust air duct (5) and being operative for selectively permitting or blocking communication to the associated second exhaust air filter (7, 18, 18'), and
    a regulating and control unit (10) connected to the valve (8), to the at least one exhaust air pressure sensor (9) and to the air supply pressure sensor (9), the regulating and control unit (10) being operative to open the valve (8) to permit communication to the second exhaust air filter (7) when the at least one exhaust air pressure sensor (9) and the air supply pressure sensor (9) sense a pressure indicative of a blockage of the first exhaust air filter (6).

2. The system for switching over the exhaust air according to claim 1, wherein
    the first and second exhaust air ducts (4, 5) are connected separately to the disposable container (3).

3. The system for switching over the exhaust air according to claim 1, wherein
    the first and second exhaust air ducts (4, 5) are connected to the disposable container (3) by a distributor piece (15, 16).

4. The system for switching over the exhaust air according to claim 1, further comprising:
    at least a third exhaust air duct (13) connected to the disposable container (3) and having a free end that is closed by a first part (20) of a two-part sterile connector (19), and
    a third exhaust air filter (18) connected to a connecting line (21) that is connected to a second part (22) of the two-part sterile connector (19), wherein the disposable container (3) is placed in communication with the third exhaust air filter (18) when the at least one exhaust air pressure sensor (9) and the air supply pressure sensor (9) senses a pressure indicative of a blockage of the first and second exhaust air filters (6, 7).

5. The system for switching over the exhaust air according to claim 1, wherein:
    the at least one exhaust air pressure sensor (9) comprises first and second pressure sensors (9) in the first and second exhaust air ducts (4, 5, 13) respectively.

6. The system for switching over the exhaust air according to claim 1, wherein
    the regulating and control unit (10) is connected by control lines (12) to the valve (8).

7. The system for switching over the exhaust air according to claim 1, wherein
    the regulating and control unit (10) is connected by sensor lines (11) to the at least one exhaust air sensor (9) and to the air supply pressure sensor (9).

8. The system for switching over the exhaust air according to claim 1, wherein
    the valve (8) is disposed upstream of the second exhaust air filters (7).

9. The system for switching over the exhaust air according to claim 1, further comprising:
    an exhaust air cooler (17) between the disposable container (3) and the exhaust air filter (6, 7).

10. The system for switching over the exhaust air according to claim 1, wherein
    the valve (8) is a pinch valve (8) that is selectively movable between the first and second exhaust air ducts (4, 5).

11. The system for switching over the exhaust air according to claim 10, further comprising:
    a replacement exhaust air filter (18') configured to be incorporated into the first exhaust air duct (4) after the first exhaust air filter (6) has been determined to be blocked, wherein, after the first exhaust air filter (6) has been determined to be blocked: the replacement filter (18') is placed in communication with the disposable container (3), the pinch valve (8) is moved from the second exhaust air duct (5) to the first exhaust air duct (4) and is closed, and the pinch valve (4) is opened after the at least one pressure sensor (9) senses a pressure indicative of a blockage of the second exhaust air filter (7).

12. The system for switching over the exhaust air according to claim 4, wherein
    the valve (8) is a pinch valve (8) that is configured to be selectively connected to and removed from the first and second exhaust air ducts (4, 5) and selectively connected to and removed from the connecting line (21), wherein the pinch valve (8) is removed from the second exhaust air duct (5), engaged between the replacement filter (18') and the two-part sterile connector (19) and closed when the second exhaust air filter (7) is not blocked and is opened to permit flow through the connecting line (21) when the at least one pressure sensor (9) detects a blockage of the second exhaust air filter (7).

* * * * *